US009902933B2

(12) United States Patent
Takahashi et al.

(10) Patent No.: US 9,902,933 B2
(45) Date of Patent: Feb. 27, 2018

(54) METHOD OF PRODUCING RETINAL PIGMENT EPITHELIAL CELL SHEET

(75) Inventors: Masayo Takahashi, Wako (JP); Satoshi Okamoto, Wako (JP); Hiroyuki Kamao, Wako (JP)

(73) Assignee: RIKEN, Wako (JP)

( * ) Notice: Subject to any disclaimer, the term of this patent is extended or adjusted under 35 U.S.C. 154(b) by 375 days.

(21) Appl. No.: 14/001,108

(22) PCT Filed: Feb. 24, 2012

(86) PCT No.: PCT/JP2012/054631
§ 371 (c)(1),
(2), (4) Date: Oct. 30, 2013

(87) PCT Pub. No.: WO2012/115244
PCT Pub. Date: Aug. 30, 2012

(65) Prior Publication Data
US 2014/0057281 A1 Feb. 27, 2014

(30) Foreign Application Priority Data
Feb. 25, 2011 (JP) .................................. 2011-040130

(51) Int. Cl.
*C12N 5/079* (2010.01)
*G01N 33/50* (2006.01)
*A61K 35/00* (2006.01)

(52) U.S. Cl.
CPC ....... *C12N 5/0621* (2013.01); *G01N 33/5005* (2013.01); *A61K 35/00* (2013.01); *C12N 2506/02* (2013.01); *C12N 2506/45* (2013.01); *C12N 2509/00* (2013.01); *C12N 2533/54* (2013.01)

(58) Field of Classification Search
CPC ................................ C12N 5/079; G01N 33/50
USPC .......................................... 435/7.1, 380, 377
See application file for complete search history.

(56) References Cited

U.S. PATENT DOCUMENTS

| 5,712,163 A | 1/1998 | Parenteau et al. |
| 2006/0153815 A1* | 7/2006 | Seyda ................. A61L 27/3604 424/93.7 |
| 2006/0177492 A1 | 8/2006 | Yunoki et al. |
| 2012/0009159 A1* | 1/2012 | Humayun .............. A61K 35/30 424/93.7 |
| 2013/0108590 A1 | 5/2013 | Takahashi et al. |
| 2015/0250828 A1 | 9/2015 | Kamao et al. |

FOREIGN PATENT DOCUMENTS

| JP | 2005-261292 A | 9/2005 |
| WO | WO 2009-127809 A1 | 10/2009 |
| WO | WO 2011/142364 A1 | 11/2011 |

OTHER PUBLICATIONS

Nagai, Nobuhiro. et al. A Method of Cell-Sheet Preparation Using Collagenase Digestion of Salmon Atelocollagen Fibrillar Gel Journal of Bioscience and Bioengineering. vol. 98, No. 6, 493-496. 2004.*
Yaji, Naoko et al. Transplantation of tissue-engineered retinal pigment epithelial cell sheets in a rabbit model. Biomaterials 30 (2009) 797-803.*
Meyer, Jason et al. Modeling early retinal development with human embryonic and induced pluripotent stem cells. PNAS. 2009. pp. 16698-16703.*
Cen (Collagen Tissue Engineering: Development of Novel Biomaterials and Applications, 2008).*
Cen, Lian et al. Collagen Tissue Engineering: Development of Novel Biomaterials and Applications. Pediatric Research. vol. 63, No. 5, 2008.pp. 492-496.*
Yaji (Transplantation of tissue-engineered retinal pigment epithelial cell sheets in a rabbit model, 2008—cited in the IDS filed on Dec. 4, 2015).*
Meyer (Modeling early retinal development with human embryonic and induced pluripotent stem cells, 2009.*
Bhatt et al., *American Journal of Ophthalmology*, 117(2): 214-221 (1994).
Chung et al., *Cell Stem Cell*, 2(2): 113-117 (Feb. 2008).
Kamao et al., *ARVO Annual Meeting Abstract Search and Program Planner*, 2011: 4024 (2011).
Kamao et al., *Stem Cell Reports*, 2(2): 205-218 (Feb. 11, 2014).
Ke et al., *Journal of Tissue Engineering and Regenerative Medicine*, 5(2): 138-145 (2011).
Nagai et al., *Journal of Bioscience and Bioengineering*, 98(6): 493-496 (2004).
Yaji et al., *Biomaterials*, 30(5): 797-803 (2009).
European Patent Office, Supplementary European Search Report in European Patent Application No. 12748831 dated (Oct. 3, 2014).
Abe et al., *Tohoku J. Exp. Med.*, 189: 295-305 (1999).
Kamao et al., *Journal of Japanese Ophthalmological Society*, 114: 200, abstract O1-019 (2010).
Maminishkis et al., *Investigative Ophthalmology Visual Science*, 47(8): 3612-3624 (2006).
Okamoto et al., *Japanese Journal of Transplantation*, 44(3): 231-235 (2009).
Osakada et al., *Nature Biotechnology*, 26(2): 215-224 (2008).
Peyman et al., *Ophthalmic Surgery*, 22(2): 102-108 (1991).
Sheng et al., *Investigative Ophthalmol. Vis. Sci.*, 36(2): 381-390 (1995).
Sonoda et al., *Nat. Protoc.*, 4(5): 662-673 (2009).
Japanese Patent Office, International Search Report in International Patent Application No. PCT/JP2012/054631 (dated Mar. 19, 2012).

(Continued)

*Primary Examiner* — Scott Long
*Assistant Examiner* — Nghi Nguyen
(74) *Attorney, Agent, or Firm* — Leydig, Voit & Mayer, Ltd.

(57) ABSTRACT

The present invention provides a method of producing a cell sheet including the following steps
(1) seeding and culturing retinal pigment epithelial cells on a collagen gel to form a cell sheet composed of the retinal pigment epithelial cells, and
(2) degrading the collagen gel with collagenase to detach the cell sheet composed of the retinal pigment epithelial cells, and the like.

6 Claims, 1 Drawing Sheet

(56) References Cited

OTHER PUBLICATIONS

Carr et al., "Protective Effects of Human iPS-Derived Retinal Pigment Epithelium Cell Transplantation in the Retinal Dystrophic Rat", *PLoS One*, 4(12): e8152 (2009).
Japanese Patent Office, International Search Report in International Patent Application No. PCT/JP2013/072589 (dated Sep. 17, 2013).
Japanese Patent Office, International Preliminary Report on Patentability in Application No. PCT/JP2013/072589 (dated Feb. 24, 2015).
Falkner-Radler et al., "Human retinal pigment epithelium (RPE) transplantation: outcome after autologous RPE-choroid sheet and RPE cell-suspension in a randomised clinical study," *Br. J. Ophthalmol.*, 95(3): 370-375 (2011).
U.S. Appl. No. 14/423,256, filed Feb. 23, 2015.
Klimanskaya et al., "Derivation and Comparative Assessment of Retinal Pigment Epithelium from Human Embryonic Stem Cells Using Transcriptomics," *Cloning and Stem Cells*, 6(3): 217-245 (2004).
Miyazaki, *Cell Culture Convincing Q&A*, Chapter 3 ("Preparation and maintenance of incubator tool and apparatus"), Question 29 ("What is coating of dish?") and Answer (Jan. 1, 2004) English translation.
Chinese Patent Office, First Office Action in Chinese Patent Application No. 201380051245.0 (dated Aug. 9, 2016).
European Patent Office, Supplementary European Search Report in European Patent Application No. 13830548 (dated Mar. 2, 2016).

* cited by examiner

253G1 (iPS-RPE) (48hr)

| (ng/well) | VEGF | PEDF |
|---|---|---|
| Apical | 8.61 | 792 |
| Basal | 24.53 | 429 |

454E2 (iPS-RPE) (48hr)

| (ng/well) | VEGF | PEDF |
|---|---|---|
| Apical | 1.65 | 644 |
| Basal | 14.81 | 473 | reference: Arvydas M, IOVS.2006;47:3612-3624 (24hr)

| (ng/well) | VEGF | PEDF |
|---|---|---|
| Apical | 8.7 | 661 |
| Basal | 14.7 | 285 |

METHOD OF PRODUCING RETINAL PIGMENT EPITHELIAL CELL SHEET

CROSS-REFERENCE TO RELATED APPLICATIONS

This patent application is the U.S. national phase of International Patent Application No. PCT/JP2012/054631, filed Feb. 24, 2012, which claims the benefit of Japanese Patent Application No. 2011-040130, filed on Feb. 25, 2011, which are incorporated by reference in their entireties herein.

TECHNICAL FIELD

The present invention relates to a production method of a cell sheet, comprising seeding retinal pigment epithelial cells on a collagen gel. The present invention also relates to a cell sheet for transplantation, comprising a cell layer formed from retinal pigment epithelial cells and a basement membrane.

BACKGROUND ART

At present, age-related macular degeneration (AMD) is one of the major causative diseases of legal blindness in advanced countries, and mainly seen in elderly citizens over 50 years of age. Age-related macular degeneration is caused by age-related changes in the macula, and largely divided into an exudative form and an atrophic form. Exudative age-related macular degeneration is a disease associated with the development of neovascular vessels from the choroid, in the macula of elderly citizens, then bleeding and exudative lesion under the retinal pigment epithelium or retina, and finally, formation of a scar tissue. Atrophic age-related macular degeneration is a disease accompanied by atrophy of the macular area and accumulation of drusen. A precursor lesion leading to exudative and atrophic age-related macular degeneration is sometimes referred to particularly as early age-related macular degeneration, and this lesion is also considered to be one pathology of age-related macular degeneration.

For the treatment of age-related macular degeneration when it is a mild exudative form, a surgical therapy such as photodynamic therapy, laser photocoagulation, stripping of neovascular vessel and the like, or a treatment method aiming at regression and removal of neovascular vessel by a drug therapy such as administration of an inhibitor of the vascular endothelial growth factor (VEGF) involved in the angiogenesis and the like can be selected. However, the aforementioned means cannot provide therapeutic effectiveness for the exudative or atrophic form that has progressed to the advanced atrophy or lack of retinal pigment epithelium (RPE). In such case, an effective treatment method is transplantation of retinal pigment epithelial cells or retinal pigment epithelium to the deficient site under the retina.

Various treatment methods by the transplantation of retinal pigment epithelial cells have been tried. It has been reported that transplantation of retinal pigment epithelial cells obtained from human fetus in the form of a cell suspension shows poor engraftment of the transplanted cells. In cases where a retinal pigment epithelial cell sheet also containing Bruch's membrane and choroid detached like a sheet from a cadaveric eye was transplanted, post-operative rejection occurred and a sufficient treatment effect was not obtained (non-patent document 1). In addition, the method utilizing a cadaveric eye has been pointed out to include an ethical problem. On the other hand, a case of improved eyesight of a patient with age-related macular degeneration has been reported, wherein used was a method including collecting the patient's own normal retinal pigment epithelial cells and choroid and transplanting them to the deficient site under the macula. However, this method places an extremely high burden on patients and an extremely high risk of surgery. While an attempt has been made to utilize the patient's own iris pigment epithelial cells collected from the patient with age-related macular degeneration for the transplantation instead of retinal pigment epithelial cells, the upper limit of the final eyesight is low and a sufficient effect has not been obtained, and moreover, the burden and risk of utilizing the patient's own cell are high (non-patent document 2). Thus, conventional treatment methods using cells collected from a cadaveric eye or the patient's own cells are not practical in terms of ethics, safety, effect and the like, and a retinal pigment epithelial cell truly usable for a transplantation treatment has been desired.

As one of the production methods of a retinal pigment epithelial cell sheet, a method including coating a cell culture substrate with an extracellular matrix and the like, and culturing retinal pigment epithelial cells thereon to form a sheet can be mentioned. For example, a cell sheet can be formed by culturing retinal pigment epithelial cells on a fibronectin-coated material, but formation of a basement membrane is not reported, and a method of taking out a sheet from a container in which the sheet was formed is not described at all (non-patent document 3). In consideration of such problems, a method of forming, in advance, a retinal pigment epithelial cell sheet by using an artificial membrane in place of a basement membrane has been developed by plural laboratories. However, an artificial membrane is feared to be a disorder for engraftment in transplantation and functional maintenance of the body. While an artificial membrane with a less biological response has also been developed, it is not suitable for transplantation since it problematically induces inflammation and rejection associated therewith, which are caused by the differences from the basement membrane produced by the cell itself in the composition, properties, rigidity and the like. Conventionally, moreover, a method of culturing a retinal pigment epithelial cell sheet having polarity has been known. However, it is only for experimental model use wherein retinal pigment epithelial cells and immortalized line derived from a living organism are/is made into a sheet in a container and directly utilized, and it has not yet enabled actual recovery of a retinal pigment epithelial cell sheet provided with a basement membrane as in living organisms from a container (non-patent document 4). There is a method of obtaining a retinal pigment epithelial cell sheet by exfoliating retinal pigment epithelial cells directly cultured on a culture dish, without using an extracellular matrix and the like. Such method of detaching cells by exfoliation cannot stabilize the shape and size of the sheet, basement membrane and the like, causes much damage on the retinal pigment epithelial cells by exfoliation, and causes, in most cases, disintegration of the shape of the sheet and scattered cells due to the exfoliation, thus failing to provide a cell sheet usable for transplantation and the like (non-patent document 5). In addition, while coating a cell culture substrate with collagen and culturing cells on the collagen has been reported, human retinal pigment epithelial cells are not used. Moreover, to increase the gel strength, a crosslinking agent needs to be added separately, which makes the method far from convenient and rapid (patent document 1). As the situation now stands, production of a retinal pigment epithelial cell sheet, which is therapeutically effective for retinal diseases such as age-related macular degeneration and the like, and convenient and stable to prepare, has still been a problem.

DOCUMENT LIST

Patent Document

Patent document 1: JP-A-2005-261292

Non-Patent Documents

Non-patent document 1: Ophthalmic Surg. 1991 Feb.; 22(2): 102-8.
Non-patent document 2: Tohoku J Exp Med. 1999 Dec.; 189(4): 295-305.
Non-patent document 3: Nat. Protoc., 4(5), 2009, 662-673.
Non-patent document 4: Invest. Ophthalmol. Vis. Sci., 47, 2006, 3612-3624.
Non-patent document 5: Invest. Ophthalmol. Vis. Sci., 36(2), 1995, 381-390.

SUMMARY OF THE INVENTION

Problems to be Solved by the Invention

The problem of the present invention is to develop a new method of producing a retinal pigment epithelial cell sheet conveniently and stably without using an artificial membrane, and provide patients with a disease associated with the lack of retinal pigment epithelium such as age-related macular degeneration and the like with a retinal pigment epithelial cell sheet for transplantation, which shows high engraftment rate and is superior in function.

Means of Solving the Problems

The present inventors produced a cell sheet by forming a collagen gel layer on a cell culture substrate, and seeding and culturing retinal pigment epithelial cells thereon. A cell sheet obtained by such method maintains a basement membrane between the collagen gel and the retinal pigment epithelial cell sheet, has cytokine secretion ability and adhesiveness between cells similar to those of retinal pigment epithelial cells in vivo, and permits easy detachment of the retinal pigment epithelial cell sheet from the cell culture substrate while maintaining the basement membrane by decomposing the collagen gel with collagenase. In addition, the cells constituting the cell sheet maintained the expression of a retinal pigment epithelial cell specific marker. The present inventors have conducted intensive studies and completed the present invention from these findings. Accordingly, the present invention provides

[1] a method of producing a cell sheet comprising the following steps
  (1) seeding and culturing retinal pigment epithelial cells on a collagen gel to form a cell sheet composed of the retinal pigment epithelial cells, and
  (2) degrading the collagen gel with collagenase to detach the cell sheet composed of the retinal pigment epithelial cells;
[2] the production method of the cell sheet of the above-mentioned [1], wherein the retinal pigment epithelial cells are cells obtained by inducing differentiation of stem cells or progenitor cells;
[3] the production method of the cell sheet of the above-mentioned [2], wherein the stem cells are ES cells or iPS cells;
[4] the production method of the cell sheet of the above-mentioned [1], wherein the concentration of collagen in the collagen gel is 0.1%-0.5%;
[5] the production method of the cell sheet of any one of the above-mentioned [1] to [4], further comprising the following step (3)
  (3) confirming the presence or absence of a basement membrane on the contact surface between the detached cell sheet and the collagen gel;
[6] a cell sheet produced by the method of any one of the above-mentioned [1] to [5];
[7] a cell sheet for transplantation, comprising a cell layer formed with retinal pigment epithelial cells obtained by inducing differentiation of stem cells or progenitor cells ex vivo, and a basement membrane secreted from said cells; and
[8] a cell sheet for screening, comprising a cell layer formed with retinal pigment epithelial cells obtained by inducing differentiation of stem cells or progenitor cells ex vivo, and a basement membrane secreted from said cells.

Effect of the Invention

According to the present invention, a retinal pigment epithelial cell sheet having a constitution having a basement membrane appearing on a surface can be prepared easily and stably. Since the cell sheet of the present invention is superior in the engraftment rate and functionality, and extremely useful for transplantation, a sheet composed of a basement membrane and retinal pigment epithelial cells can be produced and applied to patients with ophthalmic diseases such as patients with age-related macular degeneration and the like by transplantation. Particularly, when the cell to be used for culture is a retinal pigment epithelial cell derived an iPS cell, rejection in transplantation can be avoided by utilizing the patients' own cell as a source.

BRIEF DESCRIPTION OF THE DRAWINGS

FIG. 1 shows the results of the test of the cytokine secretory capacity of the retinal pigment epithelial cell sheet.

DESCRIPTION OF EMBODIMENTS

The present invention is explained in detail in the following.

The present invention provides a production method of a cell sheet, including the following steps:
(1) seeding and culturing retinal pigment epithelial cells on a collagen gel to form a cell sheet composed of the retinal pigment epithelial cells, and
(2) degrading the collagen gel with collagenase to detach the cell sheet composed of the retinal pigment epithelial cells.

While the retinal pigment epithelial cell to be seeded in step (1) may be a cell derived from any mammal as long as it is derived from a mammal (e.g., human, monkey, mouse, rat, dog, bovine, horse, swine, sheep, goat, cat, rabbit, hamster, guinea pig etc.), it is preferably a cell derived from human.

The retinal pigment epithelial cell to be seeded may be a primary cell directly collected from an eyeball, or a cell after several passages. The primary retinal pigment epithelial cells can be isolated by a known method. For example, in the case of eyeball-derived retinal pigment epithelial cells, a cadaveric eyeball is isolated, rapidly divided at the equatorial segment, the vitreous body and the retina are removed and treated with collagenase, hyaluronidase and the like as necessary, the cells are collected by scratching with a cell scraper, or treatment in trypsin or EDTA solution to liberate the cells from the Bruch's membrane, stood in a culture medium to induce adhesion to the culture dish and growth, and the cells grown in the required number are appropriately passaged with a trypsin treatment etc. to secure the cell number.

Furthermore, these cells may also be the cells obtained by inducing differentiation of undifferentiated pluripotent stem cells such as embryonic stem cell (ES cell), induced pluripotent stem cell (iPS cell) and the like, stem cells including somatic stem cells such as neural stem cell and the like, or progenitor cells including neural progenitor cell and retinal progenitor cell. The ES cell may also be an ES cell produced by nuclear reprogramming of a somatic cell. In addition, as the stem cell, the object cell may be prepared by inducing differentiation of induced pluripotent stem cell (iPS cell) reported in recent years. The iPS cell is a somatic cell-derived induced stem cell having properties equivalent to those of ES cell, which can be produced by introducing a particular nuclear reprogramming substance (nucleic acid, protein, low-molecular-weight compound etc.) into a somatic cell [Takahashi, K. and Yamanaka, S., Cell, 126: 663-676 (2006); Takahashi, K. et al., Cell, 131: 861-872 (2007)]. The conditions and medium used for differentiation of the aforementioned stem cell into the object differentiated cell may follow conventionally-known conditions and medium, or may be appropriately determined by those of ordinary skill in the art. In the present invention, a cell obtained by inducing differentiation of stem cell or progenitor cell, preferably pluripotent stem cell, is preferably used as the retinal pigment epithelial cell to be used for cell sheet, since a retinal pigment epithelial cell at an appropriate maturation stage can be prepared, and particularly, comparatively immature retinal pigment epithelial cells can be prepared and a cell sheet can be advantageously formed. In addition, when the cell sheet to be produced by the present invention is for transplantation, use of an iPS cell is preferable since a cell sheet obtained using a somatic cell of the subject, who receives transplantation, as a source of iPS cell does not have antigenicity against the subject. When a stem cell is induced to differentiate, for example, human ES cell or pluripotent stem cell such as iPS cell and the like is cultured in an ES differentiation medium added with Wnt antagonist such as Dkk-1, CKI-7 and the like and Nodal antagonist such as Lefty A, SB-431542 and the like. When cultured for a given period, Rx, Pax6 and Mitf, which are retinal progenitor cell markers, are expressed, and human retinal pigment epithelial cells can be obtained by morphological observation with an optical microscope, by confirming cells having a polygonal form and pigment [Neuroscience Letters 2009 Jul. 24 458(3) 126-31, Journal of Cell Science 2009 Sep. 1 122(Pt 17) 3169-79].

The retinal pigment epithelial cells of the present invention are cultured by seeding on a collagen gel. The collagen used for the collagen gel may be any as long as it is derived from a mammal (e.g., human, monkey, mouse, rat, dog, bovine, horse, swine, sheep, goat, cat, rabbit, hamster, guinea pig etc.) and, for example, human- or swine-derived collagen is used. Examples of the tissue derived from collagen include tendon, skin and the like. While the kind of the collagen may be any, one other than the collagen constituting the human basement membrane is preferable, one other than type-IV collagen is specifically preferable. Of these, type I collagen is preferably used. While a collagen gel can be produced by, for example, a conventionally-known production method, in the present invention, a gel composed of a collagen fiber network is produced by inducing fibrogenesis of collagen, as described in the below-mentioned Example. Since the fibrotic collagen has strength and flexibility in combination, it is easy to handle, shows good maintenance of cell proliferation and cell differentiation, and is preferable as the collagen gel to be used in the present invention. In addition, the collagen to be used in the present invention is required to maintain cells, which are seeded on the collagen gel, on the gel surface without allowing them to sink into the gel layer. As the collagen, therefore, preferred is one wherein the gel has the strength necessary for cell proliferation and, for example, collagen having a large amount of intermolecular crosslinking is preferable. As such collagen, tendon-derived collagen can be mentioned.

While the collagen concentration of the aforementioned collagen gel may be in any range as long as it can afford a gel having strength permitting engraftment and growth of retinal pigment epithelial cells, and satisfying solubility facilitating degradation by collagenase, viscosity enabling easy handling and the like, it is preferably 0.1% (W/V)-0.5% (W/V), more preferably 0.2% (W/V)-0.3% (W/V). When the collagen concentration of the collagen gel is less than 0.1% (W/V), the strength of the collagen gel becomes insufficient, and therefore, the colonization rate and cell proliferation rate of retinal pigment epithelial cells decrease. When the collagen concentration of the collagen gel exceeds 0.5% (W/V), the time of a collagenase treatment to degrade the collagen gel becomes long, which is feared to exert an adverse influence on the cells.

While the volume of a collagen gel mixed solution used for the production of the aforementioned collagen gel varies depending on the culture area and shape of a culture substrate to be used for the cell culture, it is preferably about 100 μl -about 250 μl, more preferably about 150 μl-about 200 μl, per unit area ($cm^2$). When the amount of the collagen gel mixed solution is too small, a collagen gel layer having a thin center part due to the influence of a surface tension applied to the gel surface is formed, and the sheet tends to be damaged during cutting out of the cell sheet, since the cells directly contact with a culture substrate for when the retinal pigment epithelial cells are cultured. When the amount of the collagen gel mixed solution is in excess, a thick collagen gel layer is formed on a culture substrate, which relatively reduces the amount of the culture medium, and therefore, maintenance culture is not easy to perform, collagenase treatment takes time, and damages on the cell sheet are feared.

In step (1), a cell sheet can be produced by seeding and culturing the aforementioned retinal pigment epithelial cells on the collagen gel of a cell culture substrate. The cell culture substrate in the present invention is not particularly limited as long as it is for cell culture. Examples thereof include culture containers having a porous membrane such as transwell and the like, flask, tissue culture flask, dish, petri dish, tissue culture dish, multi dish, microplate, microwell plate, multiplate, multiwell plate, chamber slide, petri dish, tube, tray, culture bag and roller bottle. Culture containers having a porous membrane are preferable, since a collagenase treatment and a cutting operation of the cell sheet are conveniently performed. For example, a commercially available transwell is preferably used. Examples of the material of the cell culture substrate in the present specification include, but are not limited to, inorganic materials such as metal, glass, ceramic, silicon and the like, organic materials represented by elastomer, plastic (e.g., polyester resin, polyethylene resin, polypropylene resin, ABS resin, nylon, acrylic resin, fluororesin, polycarbonate resin, polyurethane resin, methylpentene resin, phenol resin, melamine resin, epoxy resin, vinyl chloride resin).

The number of the retinal pigment epithelial cells to be seeded may be in any range as long as it is a cell density capable of forming a cell sheet. However, when the cell density is too low, the cell shape is bad, the culture time before reaching confluence is long, and further, the time necessary for cell maturation and coloring is long. When the cell density is too high, similarly, cell proliferation is suppressed, the culture time before reaching confluence tends to be long, and the cells may die from being overcrowded. Therefore, the density of the cells to be seeded is preferably about $4.5\times10^4$ cells/cm$^2$-about $8.5\times10^5$ cells/cm$^2$, more preferably about $8.5\times10^4$ cells/cm$^2$-about $8.5\times10^5$ cells/cm$^2$, most preferably about $4.5\times10^5$ cells/cm$^2$.

A single layer cell population (cell sheet) composed of retinal pigment epithelial cells can be formed by culturing the retinal pigment epithelial cells seeded on collagen gel in a culture medium. A culture medium can be used without particular limitation as long as it is a cell culture medium generally used in the pertinent field. For example, basal media described in "Japan tissue culture conference ed., Technique of Tissue Culture 3rd edition" page 581, published by Asakura Shoten, such as F-10 medium, F12 medium, MEM, BME medium, DMEM, oMEM, IMD medium, ES medium, DM-160 medium, Fisher medium, WE medium, RPMI1640 medium and the like, can be used. Furthermore, serum (fetal bovine serum etc.), various growth factors (EGF, FGF, HGF, PDGF etc.), antibiotic, amino acid and the like may be added to the basal medium. The pH of the medium is preferably about 6-about 8. As for culture, for example, a primary culture is performed generally at about 30-about 40° C. for about 15-about 60 hr until the retinal pigment epithelial cells become confluent. Thereafter, a secondary culture is performed for about 1 week-about 2 months while changing the medium, after which the culture is performed while aerating and stirring where necessary until formation of a cell sheet. Cells constituting the cell sheet obtained by such culture are maintained as retinal pigment epithelial cells. Maintenance of the cells as retinal pigment epithelial cells can be confirmed by detecting BEST1, RPE65, MERTK, CRALBP or the like as a specific differentiation marker.

Since the cell sheet formed in step (1) is adhered to collagen gel, for example, when it is directly used for transplantation and the like, the collagen gel is feared to prevent engraftment in a transplant recipient. If the collagen gel can be removed in advance, it is conducible to the solution of such problem. In step (2) of the present invention, the collagen gel adhering to the cell sheet formed in step (1) is degraded by collagenase. Those of ordinary skill in the art can select appropriate collagenase according to the kind of the collagen used for preparing the collagen gel. While the collagenase to be used for the degradation of the collagen gel is not particularly limited as long as it has an activity to digest collagen gel, one that does not easily degrade collagen constituting the human basement membrane (e.g., Type-IV collagen etc.) is preferable. For example, collagenase derived from a microorganism induced from *Clostridium* (*Clostridium histolyticum*) or *Streptomyces* (*Streptomyces parvulus*), which are available at a commercial level, safe and have a high enzyme activity, can be used.

As the activity of the above-mentioned collagenase, the specific activity relative to the collagen weight in the collagen gel is important rather than the activity per unit weight of collagenase and the activity per unit volume of an aqueous collagenase solution. The specific activity of the collagenase to be used for dissolving collagen gel (collagenase activity/collagen weight) is preferably not less than 0.1 U/mg. When the specific activity of the collagenase is less than 0.1 U/mg, dissolution of the collagen gel may unpreferably take too long or the gel may unpreferably be dissolved insufficiently. It is more preferably within the range of 0.1-10,000 U/mg, further preferably 1-3,000 U/mg.

In the production method of the cell sheet of the present invention, a method of acting collagenase on collagen gel is not particularly limited. A collagenase solution prepared using, as a solvent, a medium or an isotonic solution having a buffering capacity may be added to a medium, or a cell-attached collagen gel detached from a cell culture dish may be immersed in the aforementioned collagenase solution. Since a transwell is used as a cell culture substrate in the present invention, a collagen gel layer can be exposed by recovering an insert and removing the membrane on the bottom of the insert, and the exposed collagen gel is preferably immersed directly in the above-mentioned collagenase solution.

In the production method of the cell sheet of the present invention, the time of dissolving the collagen gel by collagenase is not particularly limited. When the time of acting the collagenase is too long, cell functions such as adhesion ability, proliferative capacity and the like may unpreferably degraded. While the time of dissolution by collagenase is subject to change due to specific activity of collagenase, temperature, the shape of collagen gel, collagenase treatment method and the like, it is generally 15 min-60 min. The collagenase treatment may be a single treatment or performed plural times.

The temperature during the treatment of collagen gel by collagenase in the cell sheet production method of the present invention is preferably set within the range of 10-42° C., more preferably 30-40° C., further preferably 36-38° C., since flowability of the cytoplasm of the cell generally decreases and the metabolic capacity decreases when the temperature inside living organisms becomes not more than 10° C. (about 30° C. in human), the protein is denatured and the cell function decreases when the temperature exceeds 42° C., and the optimal temperature of collagenase is mostly 37° C. and a temperature below this level prolongs the dissolution time.

In the cell sheet production method of the present invention, when the dissolution of collagen gel proceeds, the cell sheet is gradually detached from the gel, and finally liberated in the collagenase solution. To recover the cell sheet, the cell sheet may be mechanically detached from the remaining gel, or may be recovered after complete dissolution of the gel. While the mechanical detachment shortens the time until recovery of the cell sheet, since the cell sheet may be destroyed, it is preferably recovered after complete dissolution of the gel.

While the cell sheet recovered as mentioned above can be directly used for various applications, since the residual collagenase may inhibit adhesiveness between the cell sheets or adhesiveness to a tissue, it is preferably washed with a medium or an isotonic solution having a buffering capacity. The temperature during cleansing can be determined according to the collagen gel dissolution treatment by collagenase. To sufficiently remove residual collagenase, the sheet is preferably washed one or more times with a medium or an isotonic solution having a buffering capacity.

In the cell sheet obtained by the method of the present invention, cytokine specific to a retinal pigment epithelial cell is secreted with the polarity similar to that in living organisms, and transepithelial electric resistance (TER) to be an index of close adhesion bond between cells elevated as in living organisms. Therefore, it has a cell layer barrier function similar to that in living organisms. According to the method of the present invention, a cell sheet having functions similar to those in living organisms can be obtained.

In the cell sheet obtained by the method of the present invention, a tight junction is form between retinal pigment epithelial cells, and a basement membrane is formed on a contact face with the collagen gel. In the present specification, the "basement membrane" is a membrane formed from the components produced from retinal pigment epithelial cells, and means a membrane containing at least a part of the basement membrane component (hereinafter to be referred to as a "basement membrane of retinal pigment epithelial cells"). The basement membrane of the retinal pigment epithelial cell in living organisms is present as a thin film between a retinal pigment epithelial cell layer and an inner collagen layer constituting the Bruch's membrane, and is an extracellular matrix having Type-IV collagen, laminin, heparan sulfate proteoglycan (perlecan), nidogen and the like as representative components. The Bruch's membrane is a thin film between the retinal pigment epithelial cell layer and choroid, and has a 5-layer structure of a basement membrane of retinal pigment epithelial cells, an inner collagen layer, an elastin layer, an outer collagen layer, and a basement membrane of capillary lamina of choroid. The cell sheet of the present invention contains a part (basement membrane of retinal pigment epithelial cell) of the structure of the Bruch's membrane. The formation of tight junction can be confirmed by observing hexagonally-shaped closely-adhered cell form, and expression of occludin, ZO-1 and the like between cells by immunostaining.

The formation of basement membrane can be confirmed by observing expression of basement membrane markers such as laminin, heparan sulfate proteoglycan (perlecan), nidogen, or Type-IV collagen and the like on a cell surface by immunostaining, or observation with a scanning electron microscope.

Generally, retinal pigment epithelial cells cultured on a culture dish produce basement membrane components, but it is extremely difficult to detach the cells in the form of a usable retinal pigment epithelial cell sheet detached from a culture dish (Invest. Ophthalmol. Vis. Sci., 36(2), 1995, 381-390). According to the method of the present invention, retinal pigment epithelial cells together with a basement membrane produced from retinal pigment epithelial cells can be recovered as a sheet without utilizing an artificial membrane. Since retinal pigment epithelial cells form a single layer structure, when they are handled singly, the sheet structure is disintegrated and the cells are scattered into cell units. Thus, transplantation thereof as a sheet is extremely difficult. On the other hand, since the cell sheet of the present invention accompanies a basement membrane and has sufficient rigidity, it is not easily wrinkled during recovery, which makes the handling thereof extremely easy. Consequently, since mounting on a cell transplantation device and a transplantation operation can be performed smoothly, cell transplantation can be performed with minimum invasion, and both the effect and the prognosis are expected to be improved. In addition, since the cell sheet accompanies a basement membrane, it is extremely advantageous for transplantation in a disease wherein the basement membrane is simultaneously disordered. For example, age-related macular degeneration sometimes accompanies disorder of Bruch's membrane. The basement membrane in the cell sheet of the present invention compensates for the disordered part, whereby the engrafting rate of the cell sheet can be improved, and a treatment effect thereof can also be expected. Hence, the cell sheet of the present invention is preferable as a sheet for transplantation targeting a disease with a disordered basement membrane, and can be preferably utilized as a sheet for transplantation particularly targeting age-related macular degeneration.

The production method of the cell sheet of the present invention may further contain the following step (3): (3) confirming the presence or absence of a basement membrane on the contact surface between the detached cell sheet and the collagen gel.

In step (3), formation of a cell sheet having a cell layer composed of retinal pigment epithelial cells and a basement membrane can be determined by confirming the presence or absence of the basement membrane of the cell sheet. The presence or absence of the basement membrane can be confirmed by a method similar to the aforementioned confirmation of the formation of the basement membrane, for example, expression of a basement membrane marker, observation with a scanning electron microscope and the like. For detection of the basement membrane, expression of a basement membrane marker may be confirmed at any site of the cell (e.g., cytoplasm, cellular membrane, nuclear membrane and the like). Preferably, a marker expressed on a contact face with collagen gel is targeted.

The basement membrane marker in the present specification includes a transcription product, a translation product or a degradation product of a gene specifically expressed in the basement membrane. Examples of such gene include laminin, heparan sulfate proteoglycan (perlecan), nidogen, Type-IV collagen and the like. Of these, laminin, Type-IV collagen and the like, which are main components of the basement membrane, are preferably used.

A sample to be used for "confirming the presence or absence of a basement membrane on the contact surface between the detached cell sheet and the collagen gel" is not particularly limited as long as it contains a basement membrane marker (e.g., RNA, protein, degradation product thereof and the like) derived from the cell sheet (or cell) detached in step (2).

The expression of the basement membrane marker gene when the above-mentioned sample is RNA can be examined by preparing an RNA (e.g., total RNA, mRNA) fraction from the cell of the cell sheet detached in step (2) and detecting a transcription product of the marker gene contained in the fraction, or directly detecting a marker gene product in the cell without extracting RNA from the cell.

When an RNA (e.g., total RNA, mRNA) fraction is prepared from the cell, it can be prepared using a known method such as guanidine-CsCl ultracentrifugation method, AGPC method and the like. Using a commercially available RNA extraction kit (e.g., RNeasy Mini Kit; manufactured by QIAGEN etc.), total RNA with high purity can be prepared rapidly and conveniently from a trace amount of a sample. Examples of the method for detecting a transcription product of a basement membrane marker gene in an RNA fraction include a method using hybridization (Northernblot, dot blot, DNA chip analysis etc.), a method using PCR (RT-PCR, competitive PCR, real-time PCR etc.) and the like. Quantitative PCR methods such as competitive PCR, real-time PCR and the like are preferable since expression variation of a basement membrane marker gene can be detected rapidly and conveniently from a trace amount of a sample, and DNA chip analysis is preferable since expression variation of plural marker genes can be collectively detected and quantification performance can also be also improved by selecting a detection method and the like.

When Northernblot or dot blot hybridization is employed, the basement membrane marker gene can be detected using a nucleic acid (probe) capable of hybridizing with a transcription product of the gene. Examples of such nucleic acid include nucleic acid capable of hybridizing with a transcription product of a basement membrane marker gene under high stringent conditions. Examples of the "high stringent conditions" include hybridization reaction at 45° C. in 6×SSC (sodium chloride/sodium citrate), followed by washing once or more at 65° C. in 0.2×SSC/0.1% SDS and the like. Those of ordinary skill in the art can easily adjust to a desired stringency by appropriately changing the salt concentration of a hybridization solution, temperature of hybridization reaction, probe concentration, probe length, number of mismatch, hybridization reaction time, salt concentration of washing, washing temperature and the like. The nucleic acid may be DNA, RNA or DNA/RNA chimera, with preference given to DNA.

The nucleic acid to be used as a probe may be double stranded or single stranded. When double stranded, it may be double stranded DNA, double stranded RNA or DNA:RNA hybrid. When single stranded, an antisense strand can be used. While the length of the nucleic acid is not particularly limited as long as it can specifically hybridize with the target nucleic acid, it is, for example, not less than about 15 bases, preferably not less than about 30 bases. To enable detection and quantification of the target nucleic acid, the nucleic acid is preferably labeled. Examples of the label include radioisotope, enzyme, fluorescent substance, luminescence substance and the like. Examples of the radioisotope include [$^{32}$P], [$^{3}$H], [$^{14}$C] and the like. As the enzyme, a stable enzyme having a high specific activity is preferable, for example, β-galactosidase, β-glucosidase, alkaline phosphatase, peroxidase, malic acid dehydrogenase and the like. Examples of the fluorescent substance include fluorescamine, fluorescein isothiocyanate and the like. Examples of the luminescence substance include luminol, luminol derivative, luciferin, lucigenin and the like. Furthermore, biotin-(strept)avidin can also be used for binding a probe and a label.

When Northern hybridization is employed, an RNA fraction prepared as mentioned above is separated by gel electrophoresis, transferred to a membrane of nitrocellulose, nylon, polyvinylidene difluoride and the like, hybridized under the above-mentioned "high stringent conditions" in a hybridization buffer containing a labeling probe prepared as mentioned above, and the amount of the label bound to the membrane is measured for each band by a suitable method, whereby the expression level of each basement membrane marker gene can be measured.

Also in the case of dot blot, a membrane spotted with an RNA fraction is subjected to a similar hybridization reaction (performed for each marker gene), and the amount of the label at the spot is measured, whereby the expression level of each marker gene can be measured.

When DNA chip analysis is employed, for example, cDNA introduced with a suitable promoter such as T7 promoter and the like by a reverse transcription reaction is synthesized from an RNA fraction prepared as mentioned above, cRNA is synthesize using RNA polymerase (in this case, labeled cRNA is obtained by using a mononucleotide labeled with biotin and the like as a substrate). The labeled cRNA is contacted with a chip having the above-mentioned probe immobilized thereon to perform a hybridization reaction, and the amount of the label bound with each probe on the solid phase is measured, whereby the expression level of each basement membrane marker gene can be measured. This method is advantageous in terms of rapidness and convenience as the number of the detected differentiated marker genes (therefore, probes to be solid phased) increases.

On the other hand, when a marker gene is detected without extracting RNA from the cell, in situ hybridization can be used as the detection means. In this method, the cell is immobilized by treating the cell with a fixing agent, preferably a precipitation fixing agent, for example, acetone, or incubating the cell for a short time in a buffering formaldehyde solution, instead of extracting RNA from the cell. After immobilization, the cell is embedded in paraffin to form a block, and a slice cut out therefrom can be used as a sample. A well-prepared paraffin-embedded sample can be preserved at room temperature for many years. As nucleic acid to be used as a probe, those similar to the above-mentioned examples can be used. In situ hybridization is preferably used in the present invention since expression of a basement membrane marker on the contact surface between the cell and collagen gel can be directly confirmed.

Alternatively, expression of a basement membrane marker in the detached cell sheet in step (2) can be confirmed by preparing a protein fraction from the cell sheet (or cell), and detecting a translation product (i.e., marker protein) of the marker gene contained in the fraction, or directly detecting a translation product of the marker gene in the cell sheet (or cell), without extracting the protein from the cell sheet (or cell). A marker protein can be detected by an immunological measurement method (e.g., ELISA, FIA, RIA, Western blot etc.) using an antibody to each protein and, in the case of a protein showing a measurable physiological activity such as an enzyme and the like, it can be detected by measuring the physiological activity of each marker protein by a known method. Alternatively, a marker protein can also be detected by a mass spectrometry method such as MALDI-TOFMS and the like.

An antibody to each marker protein can be obtained according to a generally-used polyclonal antibody or monoclonal antibody production technique and using a marker protein or protein, or a partial peptide thereof as an immunization antigen.

When respective immunological measurement methods are applied to the examination method of the present invention, setting of special conditions, operations and the like is not necessary. A measurement system of the basement membrane marker protein can be constructed by adding general technical consideration of those of ordinary skill in the art to general conditions and operation methods in each method. As for the detail of these general technical means, compendia, books and the like can be referred to. For example, "Radioimmunoassay" edited by Hiroshi Irie (Kodansha, published in 1974), "cont. Radioimmunoassay" edited by Hiroshi Irie (Kodansha, published in 1979), "Enzyme Immunoassay" edited by Eiji Ishikawa et al. (Igaku-Shoin, published in 1978), "Enzyme Immunoassay" edited by Eiji Ishikawa et al. (2nd edition) (Igaku-Shoin, published in 1982), "Enzyme Immunoassay" edited by Eiji Ishikawa et al. (3rd edition) (Igaku-Shoin, published in 1987), "Methods in ENZYMOLOGY", Vol. 70 (Immunochemical Techniques (Part A)), ibidem, Vol. 73 (Immunochemical Techniques (Part B)), ibidem, Vol. 74 (Immunochemical Techniques (Part C)), ibidem, Vol. 84 (Immunochemical Techniques (Part D: Selected Immunoassays)), ibidem, Vol. 92 (Immunochemical Techniques (Part E: Monoclonal Antibodies and General Immunoassay Methods)), ibidem, Vol. 121 (Immunochemical Techniques (Part I: Hybridoma Technology and Monoclonal Antibodies)) (all published by Academic Press) and the like can be referred to.

The present invention also relates to a cell sheet obtained according to the aforementioned cell sheet production method, preferably, a cell sheet for transplantation comprising a cell layer formed from retinal pigment epithelial cells obtained by ex vivo differentiation induction, and a basement membrane. The retinal pigment epithelial cell sheet of the present invention is preferable as a transplantation material for the retinal treatment of patients with ophthalmic diseases. Examples of the ophthalmic disease include retinal degenerative diseases such as age-related macular degeneration disease, retinitis pigmentosa, diabetic retinopathy, retinal detachment and the like. Since the cell sheet of the present invention contains a basement membrane, it can be transplanted with a high engraftment rate for a disease involving simultaneously disordered Bruch's membrane. In addition, since the retinal pigment epithelial cell sheet of the present invention has a basement membrane made from components similar to those in living organisms, it can also be utilized for various screening purposes such as efficacy screening, toxicity evaluation and the like in the aforementioned ophthalmic diseases. For the efficacy screening for the aforementioned ophthalmic diseases, for example, the cell sheet of the present invention can be applied to screening for a substance having efficacy for the aforementioned ophthalmic diseases, according to the method described in JP-A-2007-500509. To be specific, the cell sheet of the present invention is cultured in the presence or absence of a candidate substance having efficacy under the stress conditions possibly causing the aforementioned ophthalmic diseases (e.g., light (e.g., white light, blue light; light induces death of retinal cells, particularly photoreceptor cells, and can be a macular degeneration inciting factor), A2E [retinoid N-retinylidene-N-retinyl-ethanolamine] (accumulation of A2E is considered to contribute to age-related neurodegeneration of retinal cells, particularly expression of macular degeneration), cigarette smoke aggregate (smoking is considered to be a risk factor of macular degeneration), external pressure (e.g., hydrostatic pressure; increase in the intraocular pressure is suspected to be involved in glaucoma)), and evaluation can be performed based on the number of photoreceptor that expresses rhodopsin, and by immunostaining using anti-caspase 3 antibody. For toxicity evaluation, the cell sheet of the present invention can be applied to screening for a toxic substance according to the method described in JP-A-2007-517210. To be specific, the cell sheet of the present invention is cultured in the presence or absence of a toxicity candidate substance and using the integrin marker peptide described in JP-A-2007-517210, excited with a laser at a wavelength of 488 nm, and the fluorescence at 520 nm is detected for evaluation. Moreover, the retinal pigment epithelial cell sheet of the present invention can also be utilized as a vitro model for the evaluation of various in vivo functions of retinal pigment epithelial cell such as the function relating to the maintenance of visual cells such as phagocytic capacity of photoreceptor outer segment, neuroprotective action and the like, retinal blood vessel barrier function such as pumping action, tight junction, and the like.

The cell sheet for transplantation of the present invention can be used for the treatment of the above-mentioned diseases in human and mammals other than human (e.g., monkey, mouse, rat, dog, bovine, horse, swine, sheep, goat, cat, rabbit, hamster, guinea pig etc.).

The range of the disease area to which the cell sheet for transplantation of the present invention can be applied is appropriately determined depending on the target disease, the animal species, age, sex, body weight and symptom of administration subject, and the like.

The cell sheet for transplantation of the present invention can be transplanted at once or in several portions. The application number of transplantation is determined by health-care professionals according to the disease and the guideline. For example, when the disease is age-related macular degeneration disease, the cell sheet for transplantation of the present invention may be transplanted two or more times depending on the severity thereof. When transplantation is performed plural times, the interval is not particularly limited, and a period of several days to several weeks may be placed.

The cell sheet for transplantation of the present invention is transplanted by health-care professionals according to an appropriate transplantation method in accordance with the guideline. When the cell sheet for transplantation of the present invention is transplanted under the retina, a transplantation method including delivering the sheet on a water flow from a punctured injection needle, up to the transplantation site under the retina of the eyeball, may be employed or a therapeutic apparatus exclusive for transplantation may also be used.

EXAMPLES

The present invention is explained in more detail in the following by referring to Examples, which are mere exemplifications and do not limit the scope of the present invention in any way.

Production Example 1

Preparation of Retinal Pigment Epithelial Cells

As the retinal pigment epithelial cells to be used for sheeting in the following Example 1, used were mature retinal pigment epithelial cells (253G1, K11PD2, 59M8, 59SV2, 59SV3, 59SV9, 46a, K21EV15, 101EV3, K11EV9, 454E2) obtained by inducing differentiation of iPS cell, and retinal pigment epithelial cells (hES, CMK6) obtained by inducing differentiation of ES cell, according to the method described in Neuroscience Letters 458 (2009) 126-131.

<Human iPS-Derived Retinal Pigment Epithelial Cells>

253G1 is a retinal pigment epithelial cell obtained by inducing differentiation of human iPS cell derived from a healthy human, and K11PD2 and 59M8 are retinal pigment epithelial cells induced to differentiate from human iPS cells derived from retinitis pigmentosa patients different from each other. The iPS cell were established by a method including introducing Oct3/4, Sox2, Klf4 and c-Myc genes into human skin-derived fibroblasts using retrovirus, according to the method described in Cell 131, 861-872, 2007.

59SV2, 59SV3 and 59SV9 are retinal pigment epithelial cells obtained by inducing differentiation of human iPS cells derived from the same retinitis pigmentosa patient. The iPS cells were established by a method including introducing Oct3/4, Sox2, Klf4 and c-Myc into human skin-derived fibroblasts by using Sendai virus, according to the method described in Proc. Jpn. Acad., Ser. B 85 (2.009) 348-362.

K21EV15, 101EV3, K11EV9 and 454E2 are retinal pigment epithelial cells obtained by inducing differentiation of human iPS cells derived from retinitis pigmentosa patients different from each other. The iPS cells were established by a method including introducing human Oct3/4, Sox2, Klf4, L-Myc and LIN28 into human skin-derived fibroblasts by using episomal vector, according to the method described in Nat Methods. 2011 May; 8(5): 409-12).

<Monkey iPS-Derived Retinal Pigment Epithelial Cells>

46a is a retinal pigment epithelial cell obtained by inducing differentiation of monkey (cynomolgus monkey) iPS cell, according to the method described in Jpn. J. Transplant. 44, 231-235.

<ES-Derived Retinal Pigment Epithelial Cells> hES is a retinal pigment epithelial cell obtained by inducing differentiation of human ES cell line khES-1. CMK6 is a retinal pigment epithelial cell obtained by inducing differentiation of monkey ES cell, according to the method described in Neuroscience Letters 458 (2009) 126-131.

Example 1

Production Method of Retinal Pigment Epithelial Cell Sheet

<Preparation of Collagen Gel Mixed Solution>

A: Swine tendon-derived acid-soluble Type-I collagen Cellmatrix I-A (Nitta Gelatin, 3.0 mg/ml), B: concentrated culture medium at 5-fold concentration [DMEM/F12 (Invitrogen, 12500-062, 3 g) was dissolved in MilliQ water, and total volume (50 ml) was filter-treated], and C: buffer for reconstitution [1N NaOH (50 mM, 5 ml), NaHCO$_3$ (260 mM, 2.2 g) and HEPES (200 mM, 4.77 g) were dissolved in MilliQ water, and total volume (100 ml) was filter-treated] were prepared. Under cooling, B (2 vol) was mixed (pale-yellow) with A (7 vol) without bubbling. Then, C (1 vol) was added and the mixture was mixed (pale-pink) to give a 0.21% collagen gel mixed solution.

<Preparation of Retinal Pigment Epithelial Cell Sheet>

The 0.21% collagen gel mixed solution (200 μl) was added into the insert of a 12 mm transwell insert (0.4 μm Pore Polyester membrane; Cornig, 3460), and the mixture was incubated at 37° C. for 30 min. Then, F10-10% FBS [F-10 (Sigma, N6908, 445 ml), FBS (50 ml), Penicilin-Streptomycin (Invitrogen, 15140-122, 5 ml)] was added by 1500 μl to the outside of the insert and 500 μl to the inside of the insert, and the transwell was incubated at 37° C. for 24 hr. Thereafter, the inside and outside of the insert were washed once with F10-10% FBS, respective retinal pigment epithelial cells obtained in Production Example 1 were seeded to $5 \times 10^5$ cells (F10-10% FBS, 500 μl) inside the insert, and F10-10% FBS (1500 μl) was added to the outside of the insert. The retinal pigment epithelial cells were cultured in F10-10% FBS until confluence. After reaching confluent, the medium was changed to SFRM-B27 [DMEM (Sigma, D6046, 350 ml), F12 HAM (Sigma, N6658, 150 ml), B27 (Invitrogen, 17504-044, 10 ml), 200 mM L-Glutamine (Sigma, G7513, 5 ml), Penicilin-Streptomycin (Invitrogen, 15140-122, 5 ml), bFGF (wako, 060-04543, 10 ng/ml)] (1500 μl to the outside of the insert, 500 μl to the inside of the insert, medium change was 3 times/week), and the retinal pigment epithelial cells were cultured until they showed suitable color and shape.

<Cutting Out>

After progress for 6 weeks from the start of the culture, the membrane of the insert was removed, collagenase L (Nitta Gelatin, PBS(+): Sigma, 2600 U/ml, 100 μl) was added under the insert, and the insert was incubated at 37° C. for 60 min and washed 3 times with PBS(+). SFRM-B27 was added dropwise so that the retinal pigment epithelial cell sheet would not get dry and cut into a desired size with PALM MicroBeam (ZEISS).

Example 2

Production Method of Retinal Pigment Epithelial Cell Sheet (Kind of Collagen)

In the same manner as in Example 1 except that, in the step of producing a cell sheet using 253G1 (iPS-retinal pigment epithelial cells) in Example 1, (A) swine skin-derived Type-I collagen TE (special order product: mainly containing Type-I collagen, a small quantity of Type-III collagen, Nitta Gelatin, 5 mg/ml) was used as 0.35% collagen mixed solution/well, (B) swine tendon-derived Type-I collagen T-1002 (special order product: Type-I collagen, Nitta Gelatin, 5.1 mg/ml) was used as 0.35% collagen mixed solution/well, (C) FITC-labeled collagen I (Chondrex, 1 mg/ml) was used as 0.07% collagen mixed solution/well, (D) FITC-labeled collagen I (special order, Chondrex, 3 mg/ml) was used as 0.21% collagen mixed solution/well, (E) atelocollagen (KOKEN, 3 mg/ml) was used as 0.21% collagen mixed solution/well, and (F) permeability collagen membrane for cell culture (KOKEN) was used, respectively, instead of swine tendon-derived acid-soluble Type-I collagen Cellmatrix I-A (Nitta Gelatin, 3 mg/ml) as 0.21% collagen mixed solution/well, cell sheets were produced and cut out to give retinal pigment epithelial cell sheets.

The test results of Example 1 and the cases using each of the aforementioned collagens were compared and evaluated in terms of 4 items [1. gel strength; 2. cell adhesion; 3. cell growth; 4. safety]. As a result, (A) {1. inferior; 2. equivalent; 3. inferior; 4. good}, (B) {1. good (5.1 mg/ml); 2. equivalent; 3. inferior; 4. good}, (C) {1. inferior (1 mg/ml); 2. inferior; 3. unknown; 4. unknown}, (D) {1. equivalent (3 mg/ml); 2. equivalent; 3. inferior; 4. unknown}, (E) {1. equivalent (3 mg/ml); 2. inferior; 3. unknown; 4. good}, and (F) {was not lysed by collagenase, thus unusable}. As for the gel strength, a certain level of strength is required to enable growth of retinal pigment epithelial cells. From such aspect, particularly preferable kind and concentration of collagen were the swine tendon-derived acid-soluble Type-I collagen Cellmatrix I-A of Example 1 and (B) swine tendon-derived Type-I collagen T-1002 used at the above-mentioned concentration. When the substrate does not have a certain level of strength, retinal pigment epithelium does not grow and cannot be used for the present invention.

Example 3

Production Method of Retinal Pigment Epithelial Cell Sheet (Collagen Amount)

In the same manner as in Example 1 except that, in the step of producing a cell sheet using 253G1 (iPS-retinal pigment epithelial cell) of Example 1, the amount of the collagen gel mixed solution to be used was changed to 100 μl or 300 μl from 200 μl, cell sheets were produced and cut out, whereby retinal pigment epithelial cell sheets were recovered.

As compared to Example 1, when the amount of the collagen gel mixed solution used was 100 μl, a thin collagen gel layer was formed in the center part due to an influence of the surface tension caused by the small amount of the collagen gel mixed solution and, as the culture proceeded, the seeded retinal pigment epithelial cells directly contacted the bottom membrane with ease, which caused breakage of the retinal pigment epithelial cell sheet during an operation to cut out the sheet. When the amount of the collagen gel mixed solution used was 300 µl, since the amount of the collagen gel mixed solution was high, a thick collagen gel layer was formed, which relatively reduced the amount of the medium that could be retained in the insert, and therefore, maintenance culture was not easy to perform, collagenase treatment took time, and damages on the cell sheet were feared to become greater. When the amount of the collagen gel mixed solution used was 100 µl, the cells directly contacted the membrane, and the cell sheet was disrupted from such part on removal of the membrane.

Example 4

Production Method of Retinal Pigment Epithelial Cell Sheet (Amount of Collagenase and Treatment Time)

In the same manner as in Example 1 except that, in the step of producing a cell sheet using 253G1 (iPS-retinal pigment epithelial cell) of Example 1, 1% Collagenase L (Nitta Gelatin) or Type I collagenase (Roche) was contacted with the retinal pigment epithelial cell sheet for 10 min in an amount of 10 µl, 20 min in an amount of 10 µl, 30 min in an amount of 10 µl, 20 min in an amount of 20 µl, 60 min in an amount of 20 µl, and 50 min in an amount of 30 µl, instead of 30 min in an amount of 30 µl, cell sheets were produced and cut out, whereby retinal pigment epithelial cell sheets were recovered.

As a result, when a collagenase treatment was performed for 60 min in an amount of 10 µl or 60 min in an amount of 20 µl, collagen degradation of the same level as with 30 µl for 30 min was observed.

Example 5

Production Method of Retinal Pigment Epithelial Cell Sheet (Number of Seeded Cells)

In the same manner as in Example 1 except that, in the step of producing a cell sheet using 253G1 (iPS-retinal pigment epithelial cell) of Example 1, the number of the cells to be seeded inside the insert was changed to (A) $5 \times 10^4$ cells/500 µl, (B) $1 \times 10^5$/500 µl or (C) $1 \times 10^6$/500 µl from $5 \times 10^5$ cells/500 µl, cell sheets were produced and cut out, whereby retinal pigment epithelial cell sheets were recovered.

As compared to Example 1, (A) and (B) required a longer time to reach cell confluence due to the small number of cells, and (C) showed slow growth and also tended to require a longer time to reach cell confluence.

Example 6

Basement Membrane Formed on Retinal Pigment Epithelial Cell Sheet

A cryo section (frozen section) was produced from the cell sheet produced from 253G1 (iPS-retinal pigment epithelial cell) in Example 1, and subjected to immunohistochemical staining. Formation of a tight junction was confirmed by the expression of ZO-1, and formation of a basement membrane was confirmed by the expression of laminin and Type-IV collagen. For detection of each protein, respective antibodies of rabbit anti-ZO-1 manufactured by Zymed (1:100 dilution), rabbit laminin manufactured by Abcam (1:200 dilution), and mouse anti-human collagen type IV antibody manufactured by Calbiochem (1:40) were used. Furthermore, the retinal pigment epithelial cell sheet was confirmed to have a single layer epithelial form from the state of nuclear staining using 4',6-diamidino-2-phenylindole manufactured by Molecular Probes (DAPI; 1 µg/ml).

Evaluation 1. Retinal Pigment Epithelial Specific Gene Expression Profile of Cell Sheet In the step of producing a cell sheet from 59SV3, 59SV9 (iPS-retinal pigment epithelial cells) in Example 1, the expression of BEST1, RPE65, MERTK, CRALBP in the cells constituting the sheets after lapse of 1 week, 4 weeks, 2 months, wherein the day when the medium was changed to SFRM-B27 after cell confluence was day 0, was confirmed by RT-PCR. As a result, expression of the same level as that of the positive control (human retinal pigment epithelial cell total RNA (manufactured by ScienCell, Cat NO. 6545)) was observed. Here, BEST1, RPE65, MERTK are genes specifically expressed in retinal pigment epithelial cells. CRALBP is a gene expressed in retinal pigment epithelial cells and Muller cells.

Evaluation 2. Measurement of Residual Collagen in Retinal Pigment Epithelial Sheet Cryo sections (frozen section) were produced by cutting out, before and after collagenase treatment, from respective cell sheets produced from 253G1 (iPS-retinal pigment epithelial cell) in Example 1, and subjected to immunohistochemical staining. The nucleus was stained with 4',6-diamidino-2-phenylindole (DAPI; 1 µg/ml) manufactured by Molecular Probes, and Collagen type 1 was stained with rabbit anti-human collagen type I antibody (1:40 dilution) manufactured by Calbiochem. As a result, collagen was not detected from the sheets after the collagenase treatment, and it was confirmed that collagenase removed collagen coated on the culture dish. On the other hand, collagen was detected from the sheets cut out before the collagenase treatment.

Evaluation 3. Cytokine Secretion Capability of Retinal Pigment Epithelial Cell Sheet The culture media on the Apical side and the Basal side in the transwell were recovered before the step of cutting out retinal pigment epithelial cell sheets from the cell sheets produced from 253G1 (iPS-retinal pigment epithelial cell) and 454E2 (iPS-retinal pigment epithelial cell) in Example 1, and the production amounts of VEGF and PEDF were detected by ELISA according to the method described in Arvydas M, IOVS. 2006; 47: 3612-3624. As a result, it was confirmed that, similar to the human embryo-derived retinal pigment epithelium reported in Arvydas M, IOVS. 2006; 47: 3612-3624, VEGF was mainly secreted on the Basal side, and PEDF was mainly secreted on the Apical side (FIG. 1). It was shown that the cell sheet of the present invention has cytokine secretory capability similar to that in living organisms, and is superior in functionality.

Evaluation 4. Transepithelial Electric Resistance of Retinal Pigment Epithelial Cell Sheet A strong correlation is seen between the barrier function of a cell layer and impedance, namely, transepithelial/transendothelial electric resistance (TER). A probe was placed in the media inside and outside the insert according to the method described by MILLIPORE (using Millicell ERS-2), before the step of cutting out the retinal pigment epithelial cell sheet produced from 454E2 (iPS-retinal pigment epithelial cell) in Example 1, and TER was electrically measured. As a result, TER was 640Ω·cm$^2$, and showed a high TER value like the human embryo-derived retinal pigment epithelium reported in Nature Protocols vol 4, No 5 662-673 (2009), FIG. 10. It was shown that the cell sheet of the present invention has a high barrier function similar to that in living organisms.

Evaluation 5. Transplantation of Retinal Pigment Epithelial Cell Sheet Derived from Monkey ES Cell A monkey retinal pigment epithelial cell sheet produced from monkey ES cell-derived retinal pigment epithelial cells, CMK6 in Example 1 was transplanted into one eye of a monkey according to the method described in Invest Ophthalmol Vis Sci. 1995 February; 36(2): 381-90. Before the transplantation, retinal photocoagulation was performed to disorder the retina of the eye to be subjected to transplantation. On day 28 from the transplantation into the one eye of the monkey having retinal photocoagulation macula formed therein, eye fundus photographs were taken, and images of the ocular fundus sections were produced as histological sections by using OCT (Optical coherence tomograph), based on which the condition of the retina was confirmed. As a result, no leakage of fluorescence was found by fluorescein angiography, the graft survived, and a disorder such as thinning of sensory retina and the like were not found.

Evaluation 6. Transplantation of Retinal Pigment Epithelial Cell Sheet Derived from Monkey iPS Cell A monkey retinal pigment epithelial cell sheet produced from monkey iPS cell-derived retinal pigment epithelial cells, 46a in Example 1 was transplanted under the retina of one eye for autologous transplantation and three eyes for cross transplantation according to the method described in Invest Ophthalmol Vis Sci. 1995 February; 36(2): 381-90. Up to one year post-transplantation, eye fundus photographs were taken, and images of the ocular fundus sections were produced as histological sections by using OCT (Optical coherence tomograph), based on which the condition of the retina was observed with the lapse of time. In cross transplantation, clear rejection reactions such as fibrous changes on the periphery of the graft, leakage of fluorescence by fluorescein angiography, and high brightness lesion under the retina by OCT were found. On the other hand, in autologous transplantation, such clear rejection was not observed, no leakage of fluorescence was found by fluorescein angiography, the graft survived, and a disorder such as thinning of sensory retina and the like were not found.

INDUSTRIAL APPLICABILITY

Using the method of the present invention, a retinal pigment epithelial cell sheet to be applied by transplantation to patients with age-related macular degeneration can be produced comparatively conveniently. Particularly, when the cells to be used for culture are iPS cell-derived retinal pigment epithelial cells, the patient's own cells can be utilized, which can avoid rejection in transplantation. Moreover, since the cell sheet obtained by the method of the present invention has a basement membrane made from the same components as in living organisms, a retinal pigment epithelial cell sheet closer to the state in living organisms can be reproduced, which is useful for various screening purposes.

This application is based on a patent application No. 2011-040130 filed in Japan (filing date: Feb. 25, 2011), the contents of which are incorporated in full herein.

The invention claimed is:

1. A method of producing a cell sheet comprising the following steps
   (a) seeding and culturing retinal pigment epithelial cells on a swine tendon-derived fibrotic collagen gel to form a cell sheet composed of the retinal pigment epithelial cells, and
   (b) degrading the swine tendon-derived fibrotic collagen gel with collagenase to detach the cell sheet composed of the retinal pigment epithelial cells
   wherein the concentration of collagen in the swine tendon-derived fibrotic collagen gel is 0.21-0.35%.

2. The production method of the cell sheet according to claim 1, wherein the retinal pigment epithelial cells are cells obtained by inducing differentiation of stem cells or progenitor cells.

3. The production method of the cell sheet according to claim 2, wherein the stem cells are embryonic stem (ES) cells or induced pluripotent stem (iPS) cells.

4. The production method of the cell sheet according to claim 1, further comprising the following step (c):
   (c) confirming the presence or absence of a basement membrane on the contact surface between the detached cell sheet and the swine tendon-derived fibrotic collagen gel.

5. The production method of the cell sheet according to claim 2, further comprising the following step (c):
   (c) confirming the presence or absence of a basement membrane on the contact surface between the detached cell sheet and the swine tendon-derived fibrotic collagen gel.

6. The production method of the cell sheet according to claim 3, further comprising the following step (c):
   (c) confirming the presence or absence of a basement membrane on the contact surface between the detached cell sheet and the swine tendon-derived fibrotic collagen gel.

* * * * *